US012681203B2

(12) United States Patent
Hu et al.

(10) Patent No.: US 12,681,203 B2
(45) Date of Patent: Jul. 14, 2026

(54) COAL SPONTANEOUS COMBUSTION DOWNHOLE DETECTION SYSTEM AND METHOD BASED ON SELF-POTENTIAL METHOD

(71) Applicant: SHANDONG UNIVERSITY OF SCIENCE AND TECHNOLOGY, Qingdao (CN)

(72) Inventors: Xiangming Hu, Qingdao (CN); Hao Dong, Qingdao (CN); Baiqian Wu, Qingdao (CN); Shijian Yu, Qingdao (CN); Shengli Wang, Qingdao (CN); Yong Zhou, Qingdao (CN); Wenqi Shao, Qingdao (CN); Wei Wang, Qingdao (CN); Mingyue Wu, Qingdao (CN); Fusheng Wang, Qingdao (CN); Lijun Li, Qingdao (CN); Haozhen Xuan, Qingdao (CN); Zhiyuan Yang, Qingdao (CN)

(73) Assignee: SHANDONG UNIVERSITY OF SCIENCE AND TECHNOLOGY, Qingdao (CN)

( * ) Notice: Subject to any disclaimer, the term of this patent is extended or adjusted under 35 U.S.C. 154(b) by 184 days.

(21) Appl. No.: 18/826,143

(22) Filed: Sep. 5, 2024

(65) Prior Publication Data

US 2025/0123418 A1 Apr. 17, 2025

(30) Foreign Application Priority Data

Oct. 13, 2023 (CN) .......................... 202311321729.4

(51) Int. Cl.
*G01V 3/26* (2006.01)
*E21F 17/18* (2006.01)
(Continued)

(52) U.S. Cl.
CPC .............. *G01V 3/265* (2013.01); *E21F 17/18* (2013.01); *G01N 25/50* (2013.01); *G01N 33/222* (2013.01); *G01V 3/34* (2013.01)

(58) Field of Classification Search
CPC ............................ G01N 25/50; G01N 33/222
See application file for complete search history.

(56) References Cited

FOREIGN PATENT DOCUMENTS

| CN | 107015282 A | 8/2017 |
| CN | 110531427 A | 12/2019 |

(Continued)

OTHER PUBLICATIONS

Zhang Weizhen et al., "Advance detecting system based on dual-frequency IP method for coal roadway mechanized tunneling", China Coal, vol. 38, Issue 12, Dec. 31, 2012, pp. 32-35.

*Primary Examiner* — Alesa Allgood

(57) ABSTRACT

The present invention relates to the field of coal mine concealed fire zone detection, in particular to a coal spontaneous combustion downhole detection system and method based on a self-potential method. The coal spontaneous combustion downhole detection system comprises a self-potential detection apparatus and a self-potential processing apparatus; the self-potential detection apparatus comprises measuring electrodes, a reference electrode and metal anchor rods; the measuring electrodes are arranged on a top plate of a goaf roadway, are fixed to the metal anchor rods, and are in wireless connection with the reference electrode through the metal anchor rods; the self-potential processing apparatus comprises a data processing sensor for processing potential data and an imaging sensor for converting data into images; and the measuring electrodes and the reference electrode are in wireless connection with the data processing sensor.

6 Claims, 2 Drawing Sheets

(51) Int. Cl.

*G01N 25/50*      (2006.01)
    *G01N 33/22*      (2006.01)
    *G01V 3/34*       (2006.01)

(56)           References Cited

FOREIGN PATENT DOCUMENTS

| | | | | |
|---|---|---|---|---|
| CN | 110989018 A | | 4/2020 | |
| CN | 116224443 A | * | 6/2023 | .............. G01V 3/00 |
| KR | 20030047158 A | | 6/2003 | |
| WO | 2005124395 A2 | | 12/2005 | |

* cited by examiner

COAL SPONTANEOUS COMBUSTION DOWNHOLE DETECTION SYSTEM AND METHOD BASED ON SELF-POTENTIAL METHOD

CROSS-REFERENCE TO RELATED APPLICATIONS

This application claims foreign priority of Chinese Patent Application No. 202311321729.4, filed on Oct. 13, 2023 in the China National Intellectual Property Administration, the disclosures of all of which are hereby incorporated by reference.

TECHNICAL FIELD

The present invention relates to the field of goaf concealed fire source zone detection, in particular to a coal spontaneous combustion downhole detection system and method based on a self-potential method.

BACKGROUND

The geological conditions of coal mines are complex, and fire disasters often break out in the working faces of coal mines, especially the spontaneous combustion concealed fire disasters in the goaf Due to the concealment of the high-temperature location of coal seam spontaneous combustion fire disasters and the complex direction of heat transfer in the fire zone caused by air leakage in the working face, it is difficult to detect the spontaneous combustion concealed fire disasters above the goaf at the forming preliminary stage of the fire disasters.

As the working face advances, the goaf will experience heat dissipation zone, spontaneous combustion zone, and suffocation zone at the back of the working face. The heat dissipation zone is close to the working face with high wind speed, and the residual coal is unlikely to have spontaneous combustion. The low oxygen concentration inside the suffocation zone does not form a condition for spontaneous combustion of residual coal. Both the oxygen concentration and wind speed in the spontaneous combustion zone meet the condition for spontaneous combustion of residual coal; therefore, the spontaneous combustion zone is the main zone for spontaneous combustion of residual coal in the goaf.

At present, the technologies for detecting spontaneous combustion fire disasters in coal mines comprise direct investigation method, drilling method, temperature detection method, gas detection method, and physical exploration method. The direct investigation method is to determine the concealed fire zone of coal spontaneous combustion through on-site visits and actual measurements; and the drilling method is to determine the state of a coal seam by drilling coring analysis. The direct investigation method and drilling method waste time and energy and have many limitations. As the most widely used method currently, the temperature detection method mainly comprises drilling temperature measuring method, infrared temperature measuring method, and fiber optic temperature measuring method. The temperature detection method can achieve monitoring and early warning of the development process of coal spontaneous combustion, but the arrangement of temperature sensors and the testing process are likely to be affected by the special environment of the mine. The gas detection method uses the gas released by coal spontaneous combustion to determine the degree of danger at the site of coal spontaneous combustion. However, when spontaneous combustion detection is carried out, the gas detection method is more susceptible to external interference, so that the detection depth has certain limitations. The physical exploration method mainly comprises the self-potential method, magnetic method, high-density resistivity method, etc. Each physical exploration method has its own advantages, disadvantages, and scope of use. The magnetic method and resistivity method have high accuracy in detecting closed fire zones or higher fire source temperature, but they are faced with many problems in detecting downhole high-temperature abnormal areas. With the development of technology, the technology of self-potential response characteristics in the process of coal spontaneous combustion is receiving increasing attention. Studying the changes in coal self potential is crucial for improving the accuracy of concealed fire disaster detection in coal seam spontaneous combustion.

SUMMARY

According to the present invention, the technical scheme of the coal spontaneous combustion downhole detection system and method based on a self-potential method is adopted to solve the above problems; and in addition, the present invention can detect the concealed fire source of a goaf in real time, and also can show the position of the fire zone in a more intuitive and precisely manner by collecting and processing data and then converting the data into images, thus carrying out an early warning to effectively alleviate and prevent potential risks of the fire zone.

The following technical scheme is provided in the present invention: the coal spontaneous combustion downhole detection system based on a self-potential method comprises a self-potential detection apparatus and a self-potential processing apparatus; the self-potential detection apparatus comprises measuring electrodes, a reference electrode and metal anchor rods; the measuring electrodes are arranged on a top plate of a goaf roadway, are fixed to the metal anchor rods, and are in wireless connection with the reference electrode through the metal anchor rods; the self-potential processing apparatus comprises a data processing sensor for processing potential data and a imaging sensor for converting data into images; and the reference electrode is connected to the data processing sensor.

The measuring electrodes are arranged in electrode baths and are fixed by the anchor rods; one measuring electrode is arranged in each electrode bath; the electrode baths are arranged on the top plate of a goaf roadway; and the spacing between every two adjacent electrode baths is 10 m, so that every two adjacent measuring electrodes can be spaced by 10 m.

The measuring electrodes are in wireless connection with the reference electrode through low pass filters, data acquisition cards and the metal anchor rods for signal transmission; and the measuring electrodes, the low pass filters, the data acquisition cards and the metal anchor rods are in one-to-one correspondence. the low pass filter is used for collecting self-potential signals with the frequency below 5 Hz.

The measuring electrodes and reference electrode are non-polarizing copper sulfate electrodes and are made of magnetic rods.

A coal spontaneous combustion downhole detection method based on a self-potential method comprises the following steps:

S1, digging a plurality of electrode baths in the top plate area of the goaf roadway according to the roadway length, wherein the spacing T between every two adjacent electrode baths is 10 m;

S2, welding the measuring electrodes to the metal anchor rods, and then connecting and protecting the measuring electrodes, the low pass filter and the data acquisition card sequentially;

S3, burying the measuring electrodes into the electrode baths through fixing the measuring electrodes with the metal anchor rods, and transmitting signals wirelessly;

S4, enabling the self-potential processing apparatus to give a command to each data acquisition card to collect the information of each measuring electrode, and storing the information in the data acquisition card temporarily; and S5, utilizing the metal anchor rods to enhance signal transmission to transmit the information in the data acquisition card to a data processing sensor in the self-potential processing apparatus, enabling the data processing sensor to process the information according to the collecting time, the serial number of the measuring electrodes, the size of the self-potential signal, and the relationship between the self-potential signal and temperature, and transmitting the processed data to a imaging sensor to convert the data into images.

In S2, the metal anchor rods are copper anchor rods to enhance the signal. In S5, the data processing sensor comprises processes such as data conversion, modified data processing, substantive data processing, two-dimensional inversion, mapping parsing, etc.

From the above description, it can be seen that in the scheme, the characteristic that the metal anchor rods can enhance signal transmission is utilized, and the mode that the metal anchor rods are connected to the measuring electrodes is adopted, so that the self-potential signal is transmitted to the self-potential processing apparatus to be processed through the anchor rods so as to monitor the self-potential signal in real time. Through the method, the fire disasters above the goaf can be positioned more intuitively and precisely.

Figure 1:
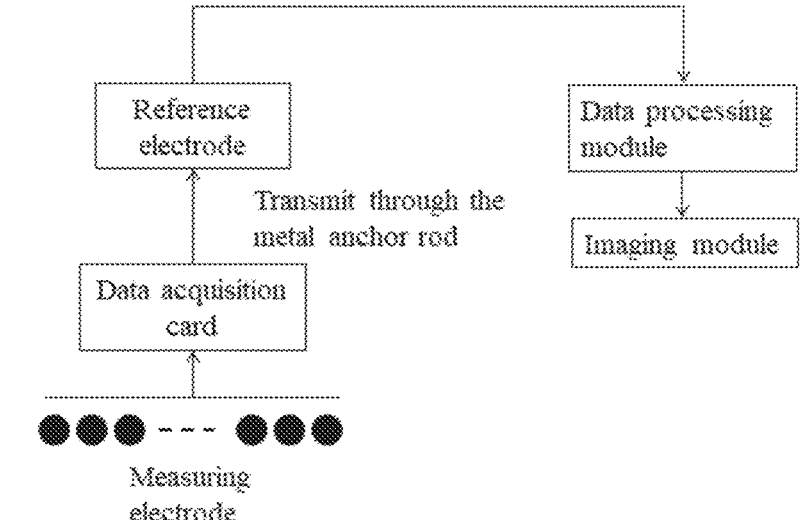
FIG. 1 is a structure diagram of the self-potential detection apparatus and the self-potential processing apparatus.
Figure 2:
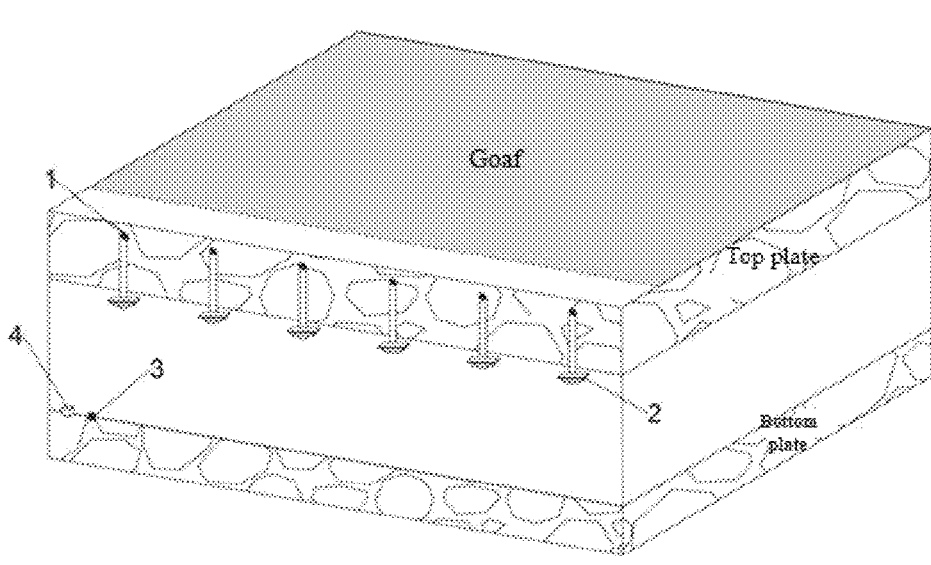
FIG. 2 is a schematic diagram for the arrangement of the coal spontaneous combustion downhole detection system at the goaf roadway of the present invention.
Figure 3:
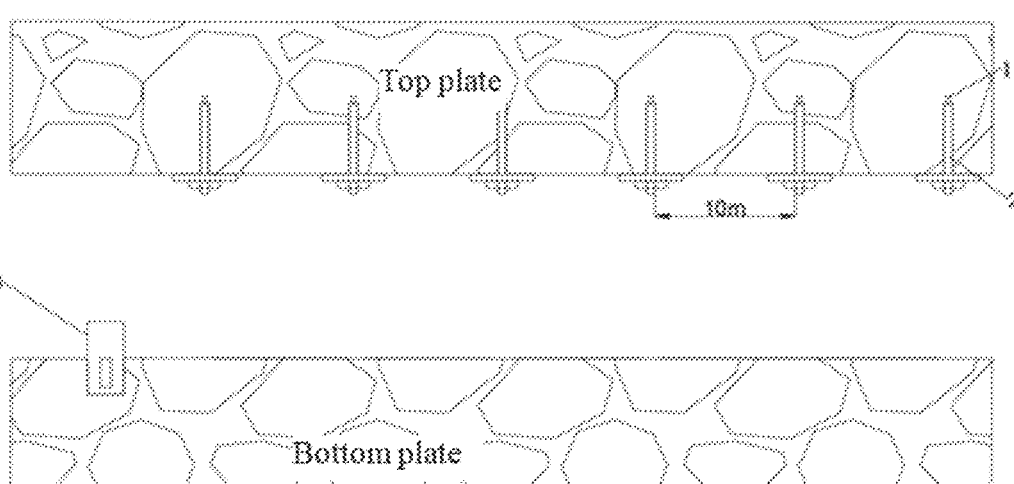
FIG. 3 is a schematic diagram for the arrangement of the self-potential detecting apparatus.
Figure 4:
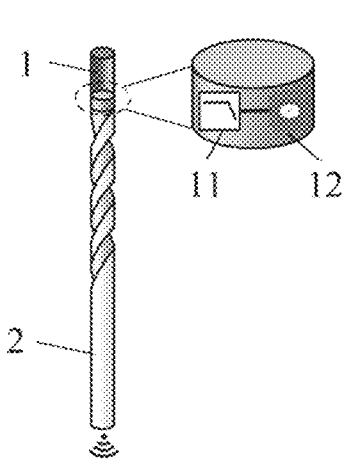
FIG. 4 is a mechanical structure diagram for the self-potential detecting apparatus.
Figure 5:
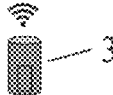
FIG. 5 is a schematic diagram for the self-potential processing apparatus.
Figure 5:
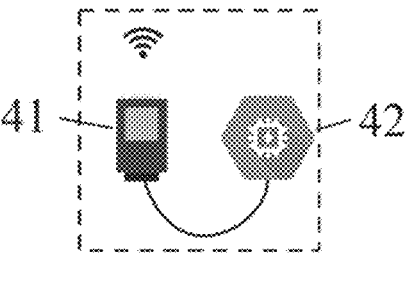

In the FIGS., 1—measuring electrode, 2—metal anchor rod, 3—reference electrode, 4—self-potential processing apparatus, 11—low pass filters, 12—data acquisition card, 41—data processing sensor, 42—imaging sensor.

DETAILED DESCRIPTION OF THE EMBODIMENTS

The technical schemes in the embodiments of the present invention will be described clearly and completely below by combining the FIGS. in the embodiments of the present invention. Obviously, the described embodiment is only an embodiment of the present invention, rather than all the embodiments. Based on the embodiments of the present invention, all other embodiments obtained by those of ordinary skill in the art without creative efforts shall fall within the protection scope of the present invention.

It should be noted that terms used herein are only for the purpose of describing specific embodiments and are not intended to limit the exemplary embodiments of the present application. As used herein, the singular form is intended to include the plural form, unless the context clearly indicates otherwise. In addition, it should further be understood that terms "comprise" and/or "include" used in this specification indicate that there are features, steps, operations, devices, components, and/or combinations thereof.

It can be seen from the FIGS. that the coal spontaneous combustion downhole detection system based on the self-potential method of the present invention comprises a self-potential detection apparatus and a self-potential processing apparatus 4; the self-potential detection apparatus comprises measuring electrodes 1, a reference electrode 3 and metal anchor rods 2; the measuring electrodes 1 are arranged on a top plate of a goaf roadway, are fixed to the metal anchor rod 2, and are in wireless connection with the reference electrode 3 through the metal anchor rods 2; and the self-potential processing apparatus 4 comprises a data processing sensor for processing potential data and a imaging sensor for converting data into images. The measuring electrodes 1 are in wireless connection with the reference electrode 3 and monitors the self-potential signal in real time; and the metal anchor rods 2 are utilized to enhance signal transmission so as to transmit signals into the self-potential processing apparatus below, and then the self-potential processing apparatus carries out data conversion, processing and inversion and finally converts data into images.

The measuring electrodes 1 are arranged in electrode baths and are buried in the top plate of the goaf roadway through fixing the measuring electrodes 1 with the metal anchor rods 2; one measuring electrode is arranged in each electrode bath; the electrode baths are arranged on the top plate of the goaf roadway; the measuring electrodes are evenly arranged; and the spacing between every two adjacent electrode baths is 10 m. the measuring electrodes and reference electrode are non-polarizing copper sulfate electrodes and are made of magnetic rods. The non-polarizing magnetic rod electrodes have stable electric property and can ensure precision and stability of monitored data.

The measuring electrodes are in electric connection with the reference electrode through low pass filters, data acquisition cards and the metal anchor rods for signal transmission; and the measuring electrodes, the low pass filters, the data acquisition cards and the metal anchor rods are in one-to-one correspondence. the low pass filter is used for collecting self-potential signals with the frequency below 5 Hz.

A coal spontaneous combustion downhole detection method based on a self-potential method adopting the coal spontaneous combustion downhole detection system comprises the following steps:

S1, digging a plurality of electrode baths in the top plate area of the goaf roadway according to the roadway length, wherein the spacing T between every two adjacent electrode baths is 10 m.

S2, welding the measuring electrodes to the metal anchor rods, and then connecting and protecting the measuring electrodes, the low pass filter and the data acquisition card sequentially; and the low pass filter and the data acquisition card can be placed in a protective box to prevent external damage.

S3, burying the measuring electrodes into the electrode baths through fixing the measuring electrodes with the metal anchor rods, arranging one measuring electrode in each electrode bath, transmitting signals wirelessly, and carrying out measurement only when all apparatuses are correctly connected.

S4, enabling the self-potential processing apparatus to give a command to each data acquisition card to collect the information of each measuring electrode, and storing the information in the data acquisition card temporarily; and S5, utilizing the metal anchor rods to enhance signal transmission to transmit the information in the data acquisition card to a data processing sensor in the self-potential processing apparatus, enabling the data processing sensor to process the information according to the collecting time, the serial number of the measuring electrodes, the size of the self-potential signal, and the relationship between the self-potential signal and temperature, and transmitting the processed data to a imaging sensor to convert the data into images.

Although the embodiments of the present invention have been shown and described, those of ordinary skill in the art can understand that various changes, modifications, replacements, and variations can be made to these embodiments without departing from the principle and spirit of the present invention, and the scope of the present invention is defined by the appended claims and equivalents thereof.

What is claimed is:

1. A coal spontaneous combustion downhole detection system based on a self-potential method, comprising a self-potential detection apparatus and a self-potential processing apparatus, wherein the self-potential detection apparatus comprises measuring electrodes, a reference electrode and metal anchor rods; the measuring electrodes are arranged on a top plate of a goaf roadway, are fixed to the metal anchor rods, and are in wireless connection with the reference electrode through the metal anchor rods;

the self-potential processing apparatus comprises a data processing sensor and an imaging sensor; and the measuring electrodes and the reference electrode are in wireless connection with the data processing sensor;

wherein the measuring electrodes are arranged in electrode baths and are fixed by the metal anchor rods; one measuring electrode is arranged in each electrode bath; the electrode baths are arranged on the top plate of a goaf roadway; and the spacing between every two adjacent electrode baths is 10 m.

2. The coal spontaneous combustion downhole detection system based on a self-potential method according to claim 1, the measuring electrodes are in wireless connection with the reference electrode through low pass filters, data acquisition cards and the metal anchor rods for signal transmission; and the measuring electrodes, the low pass filters, the data acquisition cards and the metal anchor rods are in one-to-one correspondence.

3. The coal spontaneous combustion downhole detection system based on a self-potential method according to claim 1, the measuring electrodes and reference electrode are non-polarizing copper sulfate electrodes and are made of magnetic rods.

4. A coal spontaneous combustion downhole detection method based on a self-potential method, comprising the following steps:

S1, digging a plurality of electrode baths in the top plate area of the goaf roadway according to the roadway length;

S2, welding the measuring electrodes to the metal anchor rods, and then connecting and protecting the measuring electrodes, the low pass filter and the data acquisition card sequentially;

S3, burying the measuring electrodes into the electrode baths of the top plate through fixing the measuring electrodes with the metal anchor rods, and transmitting signals wirelessly;

S4, enabling the self-potential processing apparatus to give a command to each data acquisition card to collect the information of each measuring electrode, and storing the information in the data acquisition card temporarily; and S5, utilizing the characteristic that the metal anchor rods can enhance signal transmission to transmit the information in the data acquisition card to a data processing sensor in the self-potential processing apparatus, enabling the data processing sensor to process the information according to the collecting time, the serial number of the measuring electrodes, the size of the self-potential signal, and the relationship between the self-potential signal and temperature, and transmitting the processed data to an imaging sensor to convert the data into images.

5. The coal spontaneous combustion downhole detection method based on a self-potential method according to claim 4, wherein in S2, the metal anchor rods are copper anchor rods to enhance the signal.

6. The coal spontaneous combustion downhole detection method based on a self-potential method according to claim 4, wherein the spacing T between every two adjacent electrode baths is 10 m.

* * * * *